(12) United States Patent
Okumura et al.

(10) Patent No.: US 7,920,671 B2
(45) Date of Patent: Apr. 5, 2011

(54) X-RAY CT APPARATUS AND CONTROL METHOD OF X-RAY CT APPARATUS

(75) Inventors: Miwa Okumura, Gifu (JP); Satoru Nakanishi, Utsunomiya (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 0 days.

(21) Appl. No.: 12/566,247

(22) Filed: Sep. 24, 2009

(65) Prior Publication Data
US 2010/0111393 A1 May 6, 2010

(30) Foreign Application Priority Data

Sep. 30, 2008 (JP) .................. 2008-254665

(51) Int. Cl.
*A61B 6/00* (2006.01)
(52) U.S. Cl. ............................. 378/4; 378/8
(58) Field of Classification Search .............. 378/4, 8
See application file for complete search history.

(56) References Cited

U.S. PATENT DOCUMENTS

| 4,656,584 | A  | * | 4/1987  | Katsumata      | 378/4  |
| 6,137,858 | A  | * | 10/2000 | Horiuchi       | 378/19 |
| 6,243,438 | B1 | * | 6/2001  | Nahaliel et al. | 378/19 |
| 6,445,761 | B1 | * | 9/2002  | Miyazaki et al. | 378/8  |
| 6,535,572 | B2 | * | 3/2003  | Hsieh et al.   | 378/19 |
| 6,996,206 | B2 | * | 2/2006  | Hsieh et al.   | 378/19 |
| 7,212,602 | B2 | * | 5/2007  | Tsujii         | 378/8  |
| 7,359,535 | B2 | * | 4/2008  | Salla et al.   | 382/128 |
| 7,522,695 | B2 | * | 4/2009  | Nishide et al. | 378/4  |
| 7,532,702 | B2 | * | 5/2009  | Hsieh et al.   | 378/8  |

FOREIGN PATENT DOCUMENTS

| JP | 2000-157535 | 6/2000 |
| JP | 2007-37782  | 2/2007 |
| JP | 2007-512936 | 5/2007 |
| WO | WO 2005/055829 A1 | 6/2005 |

OTHER PUBLICATIONS

L. A. Feldkamp, et al., "Practical cone-beam algorithm", J. Opt. Soc. Am. A., vol. 1, No. 6, Jun. 1984, pp. 612-619.
Henrik Turbell, "Cone-Beam Reconstruction Using Filtered Backproject", Linköping Studies in Science and Technology, Feb. 2001, 180 pages.

(Continued)

*Primary Examiner* — Edward J Glick
*Assistant Examiner* — Alexander H Taningco
(74) *Attorney, Agent, or Firm* — Oblon, Spivak, McClelland, Maier & Neustadt, L.L.P.

(57) ABSTRACT

An X-ray CT apparatus has a setting unit, a generating unit, a calculation unit, and a determination unit. The setting unit sets a required width of a group of X-ray detection elements in a row direction, which is relatively insusceptible to an influence of a cone angle of a cone-beam X-ray. The generating unit generates accumulation data by accumulating first projection data, based on first X-ray detection elements within the required width included in the group, with same channel in the row direction in preference to second projection data based on second X-ray detection elements outside the required width included in the group. The calculation unit obtains a motion amount for each heartbeat phase based on the accumulation data. The determination unit determines a specific heartbeat phase based on the motion amount for the each heartbeat phase.

20 Claims, 11 Drawing Sheets

OTHER PUBLICATIONS

Ge Wang, et al., "A General Cone-Beam Reconstruction Algorithm", IEEE Transactions on Medical Imaging, vol. 12, No. 3, Sep. 1993, pp. 486-496.

Gengsheng L. Zeng, et al., "A cone-beam tomography algorithm for orthogonal circle-and-line orbit", Phys. Med. Biol., vol. 37, No. 3, 1992, pp. 563-577.

* cited by examiner

X-RAY CT APPARATUS AND CONTROL METHOD OF X-RAY CT APPARATUS

BACKGROUND OF THE INVENTION

1. Field of the Invention

The present invention relates to an X-ray CT (computed tomography) apparatus and a control method of the X-ray CT apparatus for reconstructed image data based on projection data derived from scanning of an object using the X-ray through an electrocardiogram synchronous reconstruction method.

2. Description of the Related Art

An X-ray CT apparatus provides images as the information of an object based on the intensity of the X-ray which has transmitted the object, and plays an important role for various medical practices including diagnosis/treatment of the illness and the surgery planning.

Improvement in the time resolution of the image is one of important tasks for conducting the examination with respect to the high-rate motion using the X-ray CT apparatus, for example, the heart examination. The aforementioned task may be achieved mainly by the use of both a half reconstruction method and an electrocardiogram synchronous reconstruction method. In the methods, the half projection data set collected during rotation of the X-ray tube in the angular range of 180°+α (α: fan angle of the fan-beam X-ray) around the heartbeat phase as the center designated by the operator is extracted, and a full projection data set is generated in the angular range of 360° from the extracted half projection data set through the 2D filter using so-called parker 2D weighting factor map so as to reconstruct the image data from the full projection data set in the angular range of 360°. Note that the heartbeat phase represents the position (%) with respect to the irregular duration between R waves normalized from 0 to 100%.

In the imaging operation using the X-ray CT apparatus, the time required for the rotation at 360° or the time required for the rotation at (180°+α) for the half reconstruction is limited as the substantial time resolution from the aspect of the image reconstruction in principle. Deterioration in the image quality owing to the blur is inevitably caused by the heartbeat rate in the substantial time resolution. In most of the case, it is difficult to designate the optimum heartbeat phase, that is, it is difficult to designate the heartbeat phase with the least motion in the time width of the substantial time resolution around the heartbeat phase as the center.

Japanese Patent Application Publication (Laid-open: KOKAI) No. 2007-37782 discloses the technique for obtaining the motion amount between the heartbeat phases by adding the projection data for identifying the optimum heartbeat phase for the electrocardiogram synchronous reconstruction so as to determine the heartbeat phase with less motion based on the obtained motion amount.

As the X-ray CT apparatus, the cone-beam X-ray CT apparatus has been disclosed, which has the X-ray tube for generating the cone-beam and the oppositely disposed X-ray detector with the large plane (2D) in pairs to rotate around the object for collecting the projection data required for executing the 3D image reconstruction to be executed by the computer. In the cone-beam X-ray CT apparatus, the cone-beam artifact may interfere with the 3D image reconstruction. The FeldKamp method for reconstructing the X-ray CT image disclosed in a following Document 1 employs the exact solution type algorithm. In the aforementioned case, the precision of the reconstructed image is generally high. It is therefore employed for the image reconstruction in the multi-slice CT and the cone-beam CT with the increasing rows.

It is known that the cone-beam artifact occurs more frequently in the reconstructed image remotely located in the body axis direction besides the reconstruction surface as the rotating center at which the X-ray source rotates as disclosed in following Documents 2, 3, and 4.

Document 1: Feldkamp, L. A., Davis, L. C., Kress, J. W., "Practical cone-beam algorithm" J. Oct. Soc. Am. A1 612-619 (1984)

Document 2: Turbell, H, "Cone-beam reconstruction using filtered backprojection" Linkoping Studies in Science and Technology, Thesis (2001)

Document 3: Wang, G., Lin, T-H., Cheng, P-C., Shinozaki D. M., "A general cone-beam reconstruction algorithm" IEEE Trans. Med. Imaging 12 486-496 (1993)

Document 4: Zeng, G. L., Gullberg, G. T., "A cone-beam tomography algorithm for orthogonal circle-and-line orbit" Phys. Med. Biol. 37 563-577 (1992)

Additionally, Published Japanese translation of PCT international Publication (Laid-open: KOHYO) for patent applications No. 2007-512936, and Japanese Patent Application Publication No. 2000-157535 may be referred to as the related art.

In the heart examination using the generally employed cone-beam X-ray CT apparatus, all the data in a row direction (slicing direction) are accumulated to specify the heartbeat phase. In case of the wide cone angle for forming the detection surface of 40 mm or larger, those data are not sufficient to specify the optimum heartbeat phase. The X-ray detector with the wide detection surface formed of the X-ray detection elements of 128 rows, 160 rows or 320 rows has been developed. However, even if such detector with the array of 128-row, 160-row or 320-row is directly applied to the method for setting the optimum heartbeat phase which has been conducted using the X-ray detector with the 64-row array, it is still difficult to set the optimum heartbeat phase under the influence of the cone angle.

SUMMARY OF THE INVENTION

The present invention has taken into consideration the above-described problems, and it is a purpose of the present invention to provide an X-ray CT apparatus and a control method of the X-ray CT apparatus of the present invention which it possible to accurately set the optimum heartbeat phase with precision.

To solve the above-described problems, the present invention provides the X-ray CT apparatus comprising: an X-ray tube configured to irradiate a cone-beam X-ray to an object; an X-ray detector, configured to detect the X-ray, including a group of plural X-ray detection elements arrayed in a matrix; an electrocardiogram configured to measure a heartbeat phase of the object; a set unit configured to set a required width of the group of the X-ray detection elements in a row direction, which is relatively insusceptible to an influence of a cone angle of the cone-beam X-ray; a generation unit configured to generate accumulation data by accumulating first projection data, based on first X-ray detection elements within the required width included in the group, with same channel in the row direction in preference to second projection data based on second X-ray detection elements outside the required width included in the group; a calculation unit configured to obtain a motion amount for each heartbeat phase measured by the electrocardiogram based on the accumulation data; and a determination unit configured to determine a specific heartbeat phase based on the motion amount for the each heartbeat phase.

To solve the above-described problems, the present invention provides the control method of the X-ray CT apparatus comprising: a setting step of setting a required width of a group of X-ray detection elements in a row direction, which is relatively insusceptible to an influence of a cone angle of a cone-beam X-ray; a generating step of generating accumulation data by accumulating first projection data, based on first X-ray detection elements within the required width included in the group, with same channel in the row direction in preference to second projection data based on second X-ray detection elements outside the required width included in the group; a calculation step of obtaining a motion amount for each heartbeat phase based on the accumulation data; and a determination step of determining a specific heartbeat phase based on the motion amount for the each heartbeat phase.

DESCRIPTION OF THE PREFERRED EMBODIMENTS

An X-ray CT (computed tomography) apparatus and a control method of the X-ray CT apparatus according to an embodiment of the present invention will be described referring to the accompanying drawings. Note that the X-ray CT apparatus according to the embodiment has various types including a Rotate/Rotate type having an X-ray tube and an X-ray detector in pairs as an integrated structure rotating around an object, a Stationary/Rotate type having plural detection elements arrayed to form a ring-like shape to allow only the X-ray tube to rotate around the object. The invention is applicable to any type of the system. In the specification, the Rotate/Rotate type as the mainstream type will be described.

A mechanism for converting the incident X-ray into a charge has mainly two forms, that is, an indirect conversion for converting an X-ray into light through a phosphor such as a scintillator, and further converting the light into the charge through a photoelectric conversion element such as the photo diode, and a direct conversion which uses a electron-hole pair generated in a semiconductor by the X-ray to move to a corresponding electrode, that is, a photoconductive phenomenon.

Recently, the X-ray CT apparatus of multi-tube type having plural pairs of the X-ray tube and X-ray detector installed in a rotary ring have been increasingly put into practical use, and peripheral technology has been developed as well. The embodiment is applicable to both the X-ray CT apparatus of the known single tube type and that of multi-tube type. In the specification, the X-ray CT apparatus of single tube type will be described.

Figure 1:
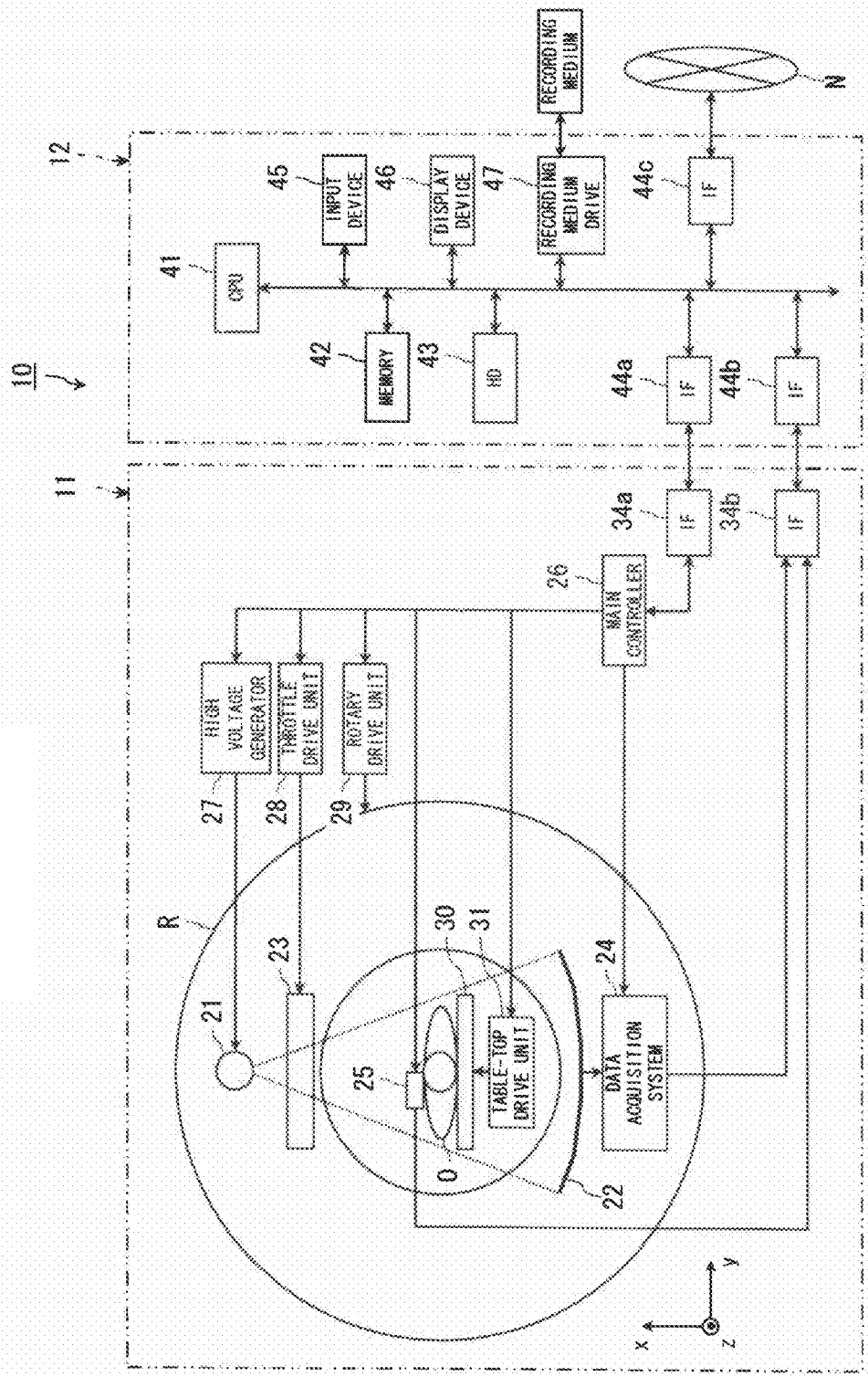
FIG. 1 is a schematic diagram showing a hardware structure which represents an X-ray CT apparatus according to an embodiment.

FIG. 1 is a schematic diagram showing a hardware structure which represents an X-ray CT apparatus according to the embodiment.

FIG. 1 shows the CT apparatus 10 according to the first embodiment. The X-ray CT apparatus 10 is mainly formed of an imaging system 11 and a control system 12. The imaging system 11 of the X-ray CT apparatus 10 is structured to generate projection data for forming the single set of volume data or plural sets of volume data in time series with respect to the imaging position of a patient (object) O. Meanwhile, the control system 12 executes generation/display of 3D image data based on the single set or plural sets of volume data in time series.

The imaging system 11 of the X-ray CT apparatus 10 has an X-ray tube 21, an X-ray detector 22, a throttle 23, a data acquisition system 24, an electrocardiogram (ECG) 25, a main controller 26, a high voltage generator 27, a throttle drive unit 28, a rotary drive unit 29, a table-top 30, a table-top drive unit 31, and IFs 34a and 34b.

The X-ray tube 21, the X-ray detector 22, the throttle 23 and the data acquisition system 24 are disposed on a rotary unit R of a gantry (not shown) of the imaging system 11. The rotary unit R is structured to allow the oppositely disposed X-ray tube 21 and the X-ray detector 22 to rotate in pairs around the patient O.

The X-ray tube 21 generates an X-ray in accordance with a tube voltage supplied from the high voltage generator 27, and irradiates a cone-beam X-ray toward the X-ray detector 22.

The X-ray detector 22 is of 2D array type (or multi-slicing type) having plural X-ray detection elements 22a in a matrix (channel direction and row direction (slicing direction)). For example, each of the X-ray detection elements 22a has a square detection surface with the size of 0.5 mm×0.5 mm.

Figure 2A:
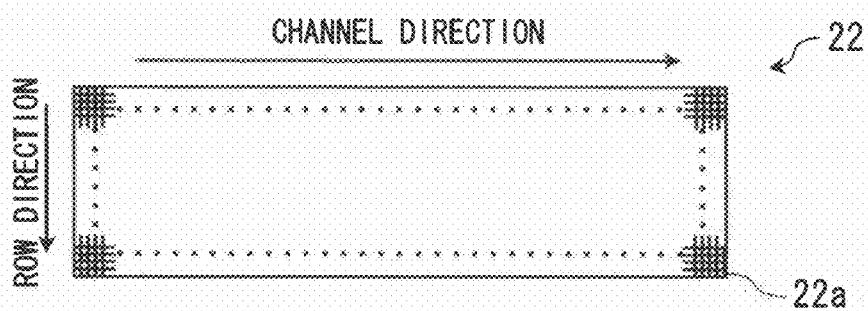
FIG. 2A is a top view showing an example of a structure of an X-ray detector.
Figure 2B:
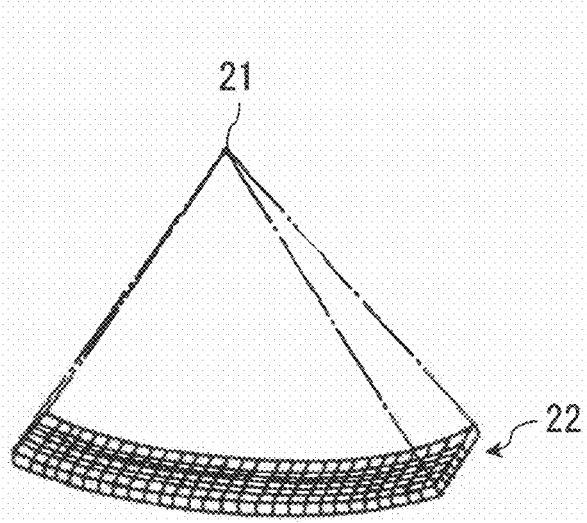
FIG. 2B is a perspective view showing the example of the structure of the X-ray detector.
Figure 2C:
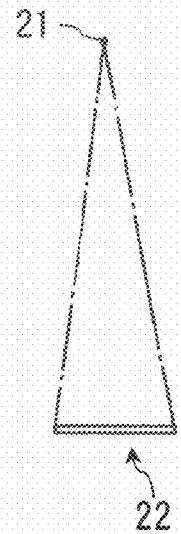
FIG. 2C is a side view showing the example of the structure of the X-ray detector.

FIG. 2A is a top view showing an example of a structure of the X-ray detector 22. FIG. 2B is a perspective view showing the example of the structure of the X-ray detector 22. FIG. 2C is a side view showing the example of the structure of the X-ray detector 22.

For example, the X-ray detector 22 is formed of plural X-ray detection elements 22a arrayed with 916 channels in the channel direction and 84 rows, 128 rows, 160 rows, or 320 rows in the row direction.

The throttle 23 shown in FIG. 1 is controlled by the throttle drive unit 28 to adjust the range of the X-ray to which the patient O is exposed in the slicing direction. That is, an opening of the throttle 23 is adjusted by the throttle drive unit 28 so as to change the X-ray exposure range in the row direction.

The data acquisition system 24 is generally called DAS for amplifying the signal output from the X-ray detector 22 for each channel, and further converting the signal into the digital signal. The converted raw data are supplied to the external control system 12 via the IF 34b of the imaging system 11.

The electrocardiogram 25 has a not shown electrocardiograph electrode, a not shown amplifier and a not shown A/D (analog to digital) conversion circuit. The electrocardiogram 25 allows the amplifier to amplify electrocardiographic waveform data as an electric signal sensed by the electrocardiograph electrode, and removes noise from the amplified signal to be converted into the digital signal. The electrocardiogram 25 is set to the patient O.

The main controller 26 controls the data acquisition system 24, the electrocardiogram 25, the high voltage generator 27, the throttle drive unit 28, the rotary drive unit 29 and the like based on a control signal input from the control system 12 via the IF 34a.

The high voltage generator 27 supplies the power required for the X-ray exposure to the X-ray tube 21 under the control of the main controller 26. The high voltage generator 27 has a not shown high voltage transformer, a not shown filament heating converter, a not shown rectifier, and a not shown high voltage switching unit.

The throttle drive unit 28 is controlled by the main controller 26 to adjust the X-ray exposure range of the throttle 23 in the row direction.

The rotary drive unit 29 is controlled by the main controller 26 to rotate the rotary unit R around a hollow portion continuously while maintaining the positional relationship of the rotary unit R.

The patient O lies on the table-top 30.

The table-top drive unit 31 is controlled by the main controller 26 to move the table-top 30 along the row direction. An opening is formed at a center of the rotary unit R, into which the patient O lying on the table-top 30 is moved. Note that a direction in parallel with a rotary center axis of the rotary unit R is designated as a z-axis direction (row direction). A plane orthogonal to the z-axis direction is defined by an x-axis direction and a y-axis direction.

The IFs 34a, 34b are formed of connectors each adapted to a parallel connection specification or a serial connection specification for executing a communication control in accordance with the respective specifications. The IFs 34a, 34b are connected to respective IFs 44a, 44b of the control system 12 for communication thereamong.

The control system 12 of the X-ray CT apparatus 10 is mainly formed of a computer, and is capable of inter-communicating with a network N such as LAN as the core system in hospital. The control system 12 is mainly formed of basic hardware such as a CPU (central processing unit) 41 as a processor, a memory 42, a HD (hard disk) 44, IFs 44a, 44b, 44c, an input device 45 and a display device 46. The CPU 41 is inter-connected to the respective hardware components of the control system 12 via a bus as a common signal transmission path. The control system 12 may be provided with a recording medium drive 47.

The CPU 41 is a control unit with an integrated circuit (LSI) structure formed by enclosing an electronic circuit formed of a semiconductor into a package with plural terminals. In response to the command input by an operator, for example, doctor through the input device 45, the CPU 41 executes a program stored in the memory 42. Alternatively, the CPU 41 loads the program recorded in the HD 43, the program transferred from the network N to be received by the IF 44c, and installed in the HD 43, or the program read from the recording medium installed in the recording medium drive 47 in the memory 42 so as to be executed.

The memory 42 is a data storage unit which serves as a ROM (read only memory) and a RAM (random access memory). The memory 42 is used for storing IPL (initial program loading), BIOS (basic input/output system) and data, or temporarily storing a work memory and the data of the CPU 41.

The HD 43 is a data storage unit having a metal disk onto which a magnetic material is applied or deposited built in a reader (not shown) so as not to be detachable. The HD 43 is the data storage unit for storing the program installed in the control system 12 (OS (operating system) in addition to an application program) and the data. More graphic may be applied for displaying information to the operator to allow the OS to supply GUI (graphical user interface) for executing a basic operation through the input device 45.

The IFs 44a, 44b, 44c are structured by the connectors each adapted to the parallel connection specification or the serial connection specification for executing the communication control in accordance with the respective specifications. The IFs 44a, 44b are used for communication with the imaging system 11, and connected to the IFs 34a, 34b of the imaging system 11, respectively. The IF 44c has a function to be connected to the network N, thus allowing the control system 12 to be connected to the network N from the IF 44c.

The input device 45 is a pointing device which can be operated by the operator. The input signal in accordance with the operation is sent to the CPU 41.

The display device 46 includes a not shown image synthesizing circuit, a not shown MUX (multiplexer), a not shown storage memory, a not shown display memory (VRAM: video random access memory), a not shown D/A (digital to analog) conversion circuit, a not shown video encoder, a not shown monitor and the like. The image synthesizing circuit generates display data formed by synthesizing a reconstructed image with character information of various parameters and scales, and outputs the display data to the MUX. The MUX appropriately switches the display data output for avoiding flickering of the display on the monitor caused by the conflict between the output to the storage memory and the output to the display memory. The storage memory stores the respective display data for each reconstructed image output from the MUX as the video file such as AVI (audio video interleaving) file. Meanwhile, the reconstructed image output from the MUX is temporarily stored as the image data.

The D/A conversion circuit converts the display data output from the MUX or the VRAM into the analog signal. The video encoder subjects the display data to the predetermined encoding process so as to output the video signal to the monitor. The monitor is formed of a liquid crystal display, a CRT (cathode ray tube) or the like to display the display data sequentially.

The recording medium drive 47 which allows the recording medium to be detachable reads the data (including the program) stored in the recording medium to be output onto the bus, and writes the data supplied via the bus into the recording medium. The aforementioned recording medium may be provided as so-called package software.

Figure 3:
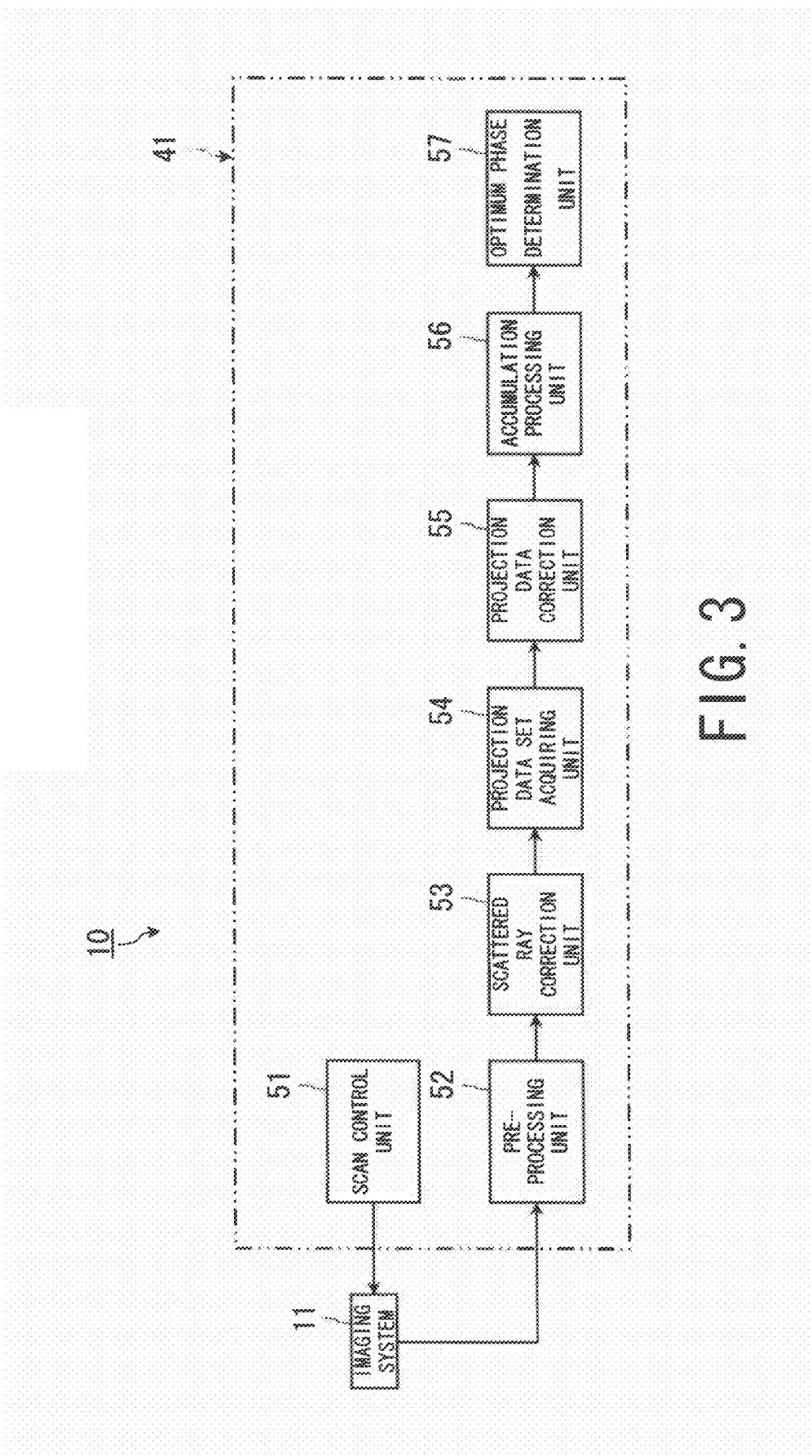
FIG. 3 is a block diagram showing functions of the X-ray CT apparatus according to a first embodiment.

FIG. 3 is a block diagram showing functions of the X-ray CT apparatus 10 according to a first embodiment.

Upon execution of the program by the CPU 41 shown in FIG. 1, the X-ray CT apparatus 10 functions as a scan control unit 51, a pre-processing unit 52, a scattered ray correction unit 53, a projection data set acquiring unit 54, a projection data correction unit 55, an accumulation processing unit 56, and an optimum phase determination unit 57, respectively. The respective units 51 to 57 for forming the X-ray CT apparatus 10 are activated by the CPU 41 for executing the program. However, the structure is not limited to the aforementioned embodiment. All or a part of the units 51 to 57 for forming the X-ray CT apparatus 10 may be installed therein as the hardware.

The scan control unit 51 has a function to control the main controller 26 of the imaging system 11 so as to execute both scanning and acquiring of the electrocardiographic waveform data.

The pre-processing unit 52 generates the projection data by subjecting the raw data input from the data acquisition system 24 of the imaging system 11 to a logarithmic conversion process and such a correction process as a sensitivity correction.

The scattered ray correction unit 53 has a function to subject the projection data input from the pre-processing unit 52 to a process for eliminating a scattered ray. The scattered ray correction unit 53 eliminates the scattered ray based on the projection data value in an X-ray exposure range. Specifically, the projection data subjected to the scattered ray correction or the scattered ray estimated based on the value size of the adjacent projection data will be subtracted from target projection data so as to execute the scattered ray correction. The projection data output from the scattered ray correction unit 53 are correlated with the electrocardiographic waveform data formed by the electrocardiogram 25 and stored in the data storage unit such as the HD 43. The projection data output from the scattered ray correction unit 53 are correlated with codes which represents a view, a channel number, a row number and position information with respect to the table-top 30.

The projection data set acquiring unit 54 has a function to acquire a half projection data set P[n] at (180°+α) with respect to a heartbeat phase variable n as a center from the projection data generated by the scattered ray correction unit 53. In other words, the projection data set acquiring unit 54 extracts the half projection data set P[n] at (180°+α) with respect to the heartbeat phase variable n as the center from the series of data (data called sinogram arrayed along a time-axis and the channel-axis) on the time-axis collected through the scanning. Note that the projection data set is defined as the projection data group required for reconstructing a single image. Under the half reconstruction method, such data exist in an angular range of (180°+α) with respect to the variable n of the specific phase as the center. In the following example, the projection data set acquiring unit 54 extracts the data in a single heartbeat duration. The projection data in plural different heartbeat durations corresponding to the heartbeat phase variable n may be synthesized to form the half projection data set P[n] for forming the single image.

In addition, the "n" denotes the variable for simply identifying the heartbeat phase. For example, if the heartbeat cycle is divided by an interval of 2%, the n takes 0, 1, 2, 3, ..., 49 and 50 corresponding to the respective heartbeat phases of 0%, 2%, 4%, 6%, ..., 98% and 100%. In the following description, the heartbeat cycle is divided by the interval of 2% (n=0 to 50).

The projection data correction unit 55 has a function to generate a full projection data set FP[n] at 360° based on the half projection data set P[n] acquired by the projection data set acquiring unit 54. The projection data correction unit 55 subjects the half projection data set P[n] to a 2D filter using so-called parker 2D weighting factor map to generate the full projection data set FP[n] having the difference with respect to the number of backprojection for each pixel of the reconstructed image compensated.

The accumulation processing unit 56 has a function to set a predetermined width W of the X-ray detector 22 in the row direction, which is relatively insusceptible to the influence of a cone angle of the cone-beam X-ray. The accumulation processing unit 56 has a function to obtain accumulation data by subjecting first projection data based on a first X-ray detection element 22a1 within the set required width W to an accumulation process (simple addition, weighted addition) with the same channel in the row direction in preference to second projection data based on a second X-ray detection element 22a2 outside the required width W on the basis of the full projection data set FP[n] generated by the projection data correction unit 55 so as to generate a full accumulation data set FBP[n] at 360°. In other words, the accumulation processing unit 56 subjects the plural first projection data to the accumulation process in preference to the second projection data within the required width in the row direction to provide a predetermined thickness in the row direction.

For example, the accumulation processing unit 56 sets the weighting to the second projection data based on the second X-ray detection element 22a2 to 0, and accumulates only the first projection data based on the first X-ray detection element 22a1 in the row direction. Alternatively, the accumulation processing unit 56 applies a relatively large weighting to the first projection data based on the first X-ray detection element 22a1, while applying a relatively small weighting to the second projection data based on the second X-ray detection element 22a2. The weighted data are accumulated in the row direction.

Figure 4:
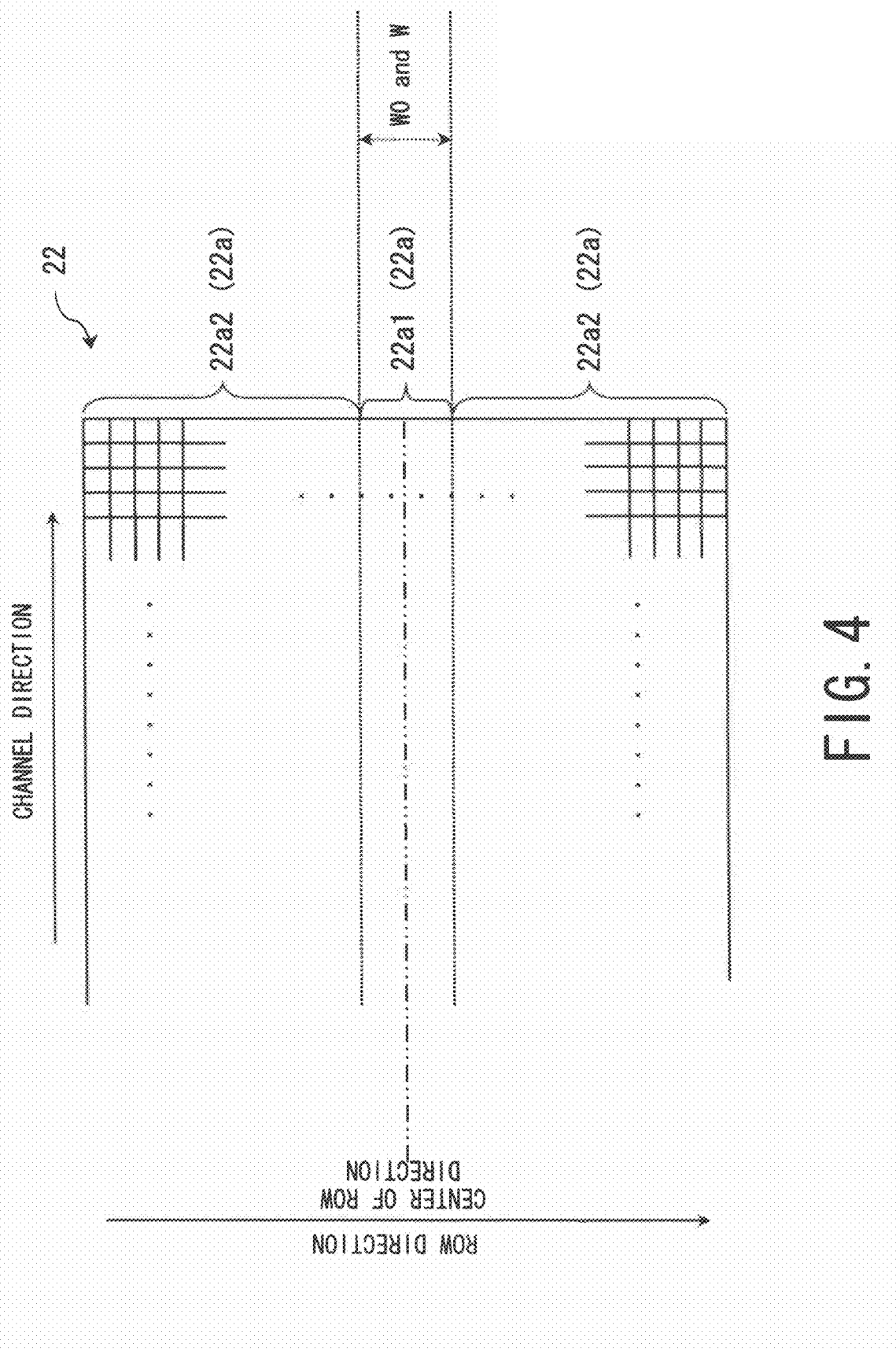
FIG. 4 is an enlarged top view showing a first example of the X-ray detector with a required width in a row direction, which is relatively insusceptible to influence of a cone angle of a cone-beam X-ray.

FIG. 4 is an enlarged top view showing a first example of the X-ray detector 22 with the required width W in the row direction, which is relatively insusceptible to the influence of the cone angle of the cone-beam X-ray.

Referring to FIG. 4, the accumulation processing unit 56 sets a reference width W0 (for example, 8 mm) in the row direction which is relatively insusceptible to the influence of the cone angle of the cone-beam X-ray from the maximum number (for example, 84-row, 128-row, 160-row or 320-row) of rows of the X-ray detection elements 22a for forming the X-ray detector 22. The accumulation processing unit 56 then sets the required width W (for example, 8 mm) in the row direction which accords with the reference width W0 in the row direction. Note that a center of the X-ray detector 22 in the row direction is considered as being the most insusceptible to the influence of the cone angle. So the accumulation processing unit 56 sets the reference width W0 in the row direction while centrally locating the center of the X-ray detector 22 in the row direction. The X-ray detection element 22a is formed of the first X-ray detection element 22a1 within the required width W in the row direction and the second X-ray detection element 22a2 outside the required width W in the row direction.

Figure 5:
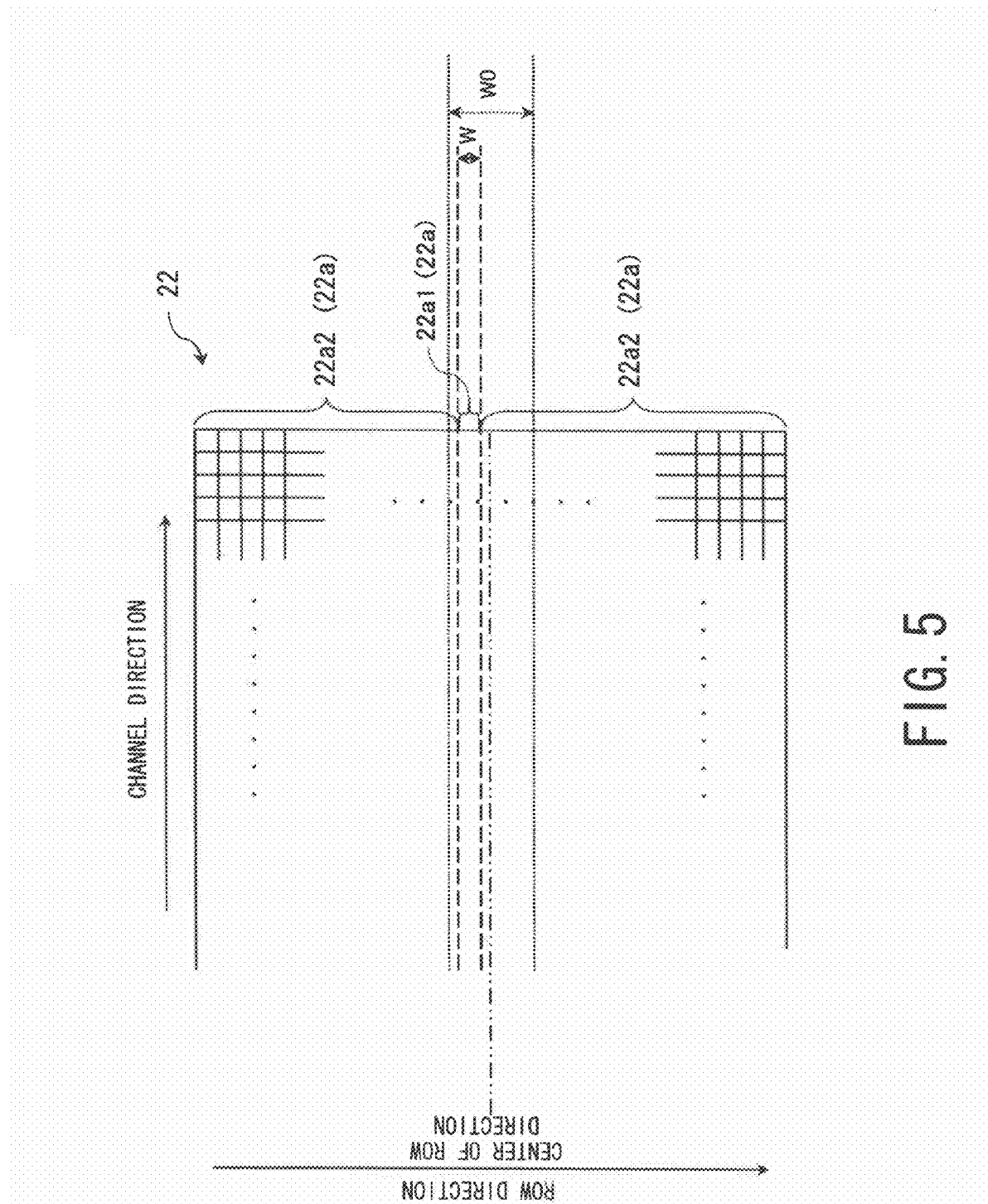
FIG. 5 is an enlarged top view showing a second example of the X-ray detector with the required width in the row direction, which is relatively insusceptible to the influence of the cone angle of the cone-beam X-ray.

FIG. 5 is an enlarged top view showing a second example of the X-ray detector 22 with the required width W in the row direction, which is relatively insusceptible to the influence of the cone angle of the cone-beam X-ray.

Referring to FIG. 5, the accumulation processing unit 56 sets the required width W in the row direction so as not to accord with the reference width W0 in the row direction.

The optimum phase determination unit 57 shown in FIG. 3 has a function to determine an optimum phase based on the full accumulation data set FBP[n] generated by the accumulation processing unit 56. Specifically, the optimum phase determination unit 57 obtains difference data between accumulation data with corresponding views and channel numbers in two full accumulation data sets with different heartbeat phase variables, which are generated by the accumulation processing unit 56. A difference data set Y[n] at 360° as the group of the difference data is generated. For example, the optimum phase determination unit 57 obtains the difference between the full accumulation data set FBP[n] and 2-phase previous full accumulation data set FBP[n−2] together with the views and the channels to generate the difference data set Y[n] with the heartbeat phase variable n.

Figure 6:
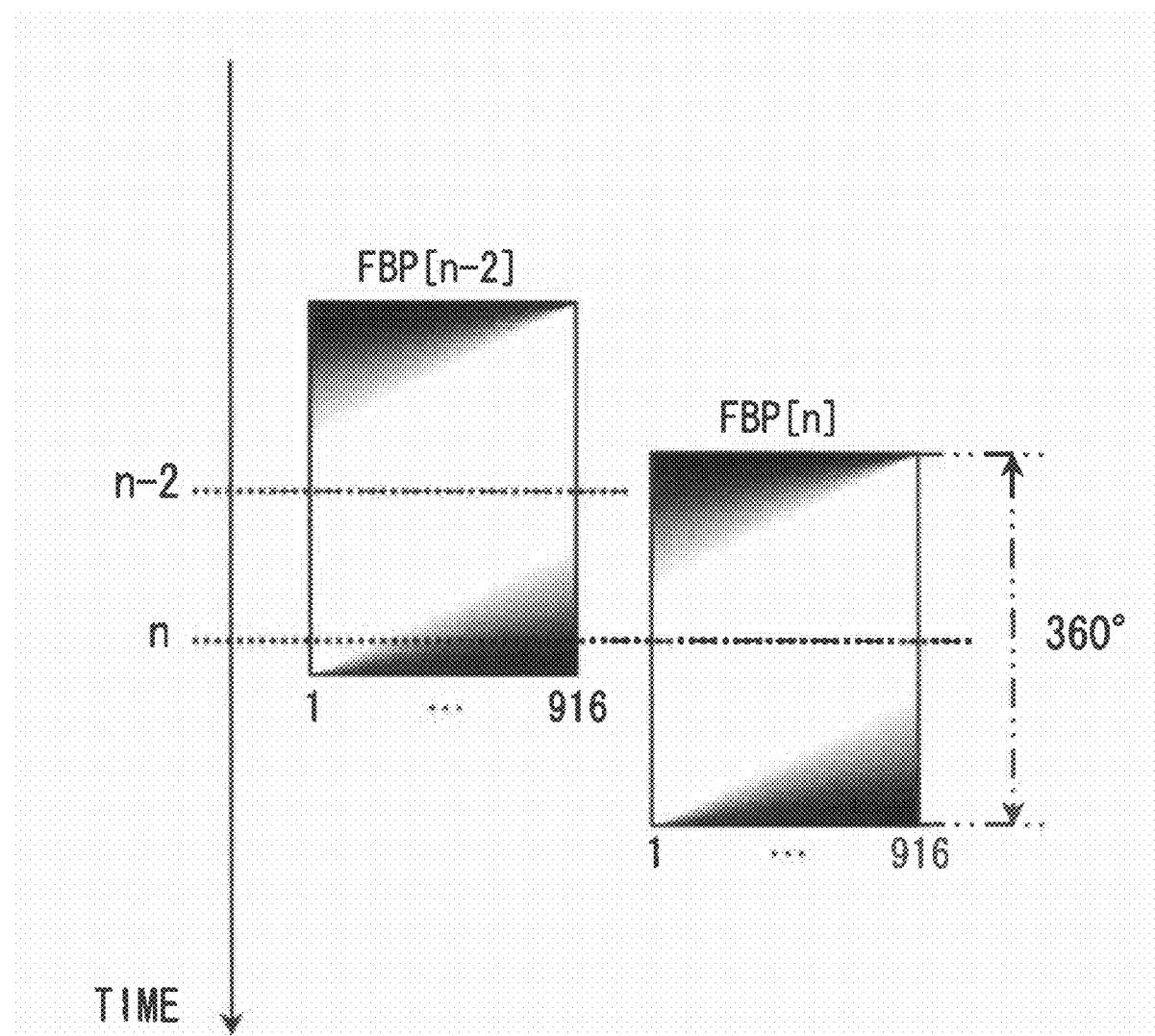
FIG. 6 is a diagram showing an example of a relationship between full accumulation data sets and a time.

FIG. 6 is a diagram showing an example of a relationship between the full accumulation data sets FBP[n], FBP[n−2], and a time.

The Y-axis of the graph shown in FIG. 6 represents time (view of the respective full accumulation data sets), and X-axis for the data sets represents the channel direction of the X-ray detector 22. The optimum phase determination unit 57 generates the difference data set Y[n] between the full accumulation data set FBP[n] and the full accumulation data set FBP[n−2] based on the projection data set P[n−2] shown in FIG. 6.

The optimum phase determination unit 57 shown in FIG. 3 calculates an absolute sum total value ST[n] based on the difference data for all channels for forming the difference data set Y[n] (difference data corresponding to the respective views and channel numbers). The absolute sum total value ST[n] is an index indicating the cardiac motion amount. Besides the absolute sum total value based on the difference data for forming the difference data set Y[n], the amount of such motion may be obtained by the other method. For example, the sum total value may be calculated by localizing the width region corresponding to a ROI (region of interest). Alternatively, such value may be derived as a square sum rather than the absolute sum total value.

Figure 7:
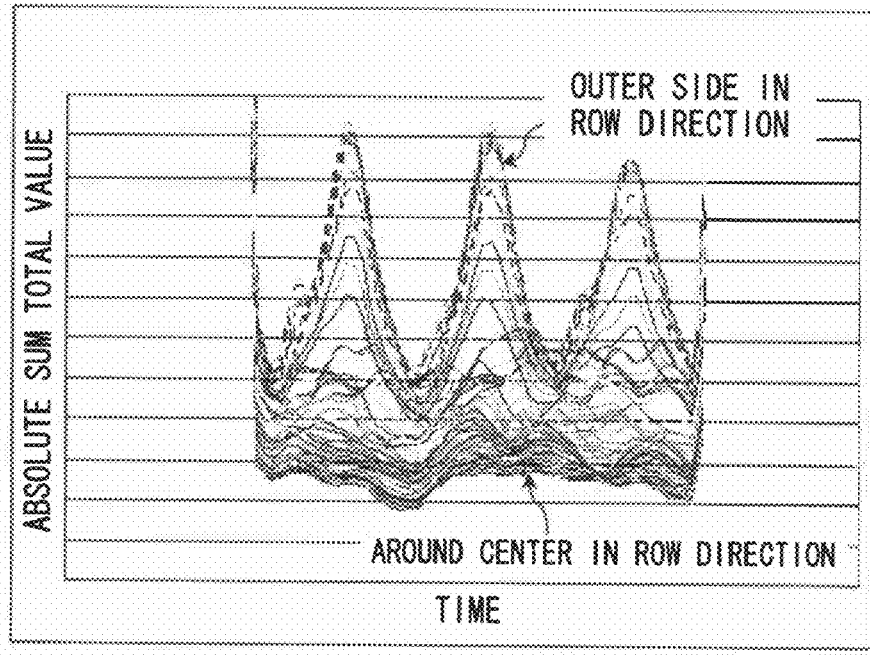
FIG. 7 is an exemplary time profile showing a first sample of an absolute sum total value for each row.

FIG. 7 is a time profile showing a first sample of the absolute sum total value for each row. The absolute sum total value is calculated based on the difference data between the projection data with corresponding views, channel numbers and the row numbers in two full projection data sets with different heartbeat phase variables without accumulating the full projection data sets FP[n] of all rows in the row direction.

Figure 8:
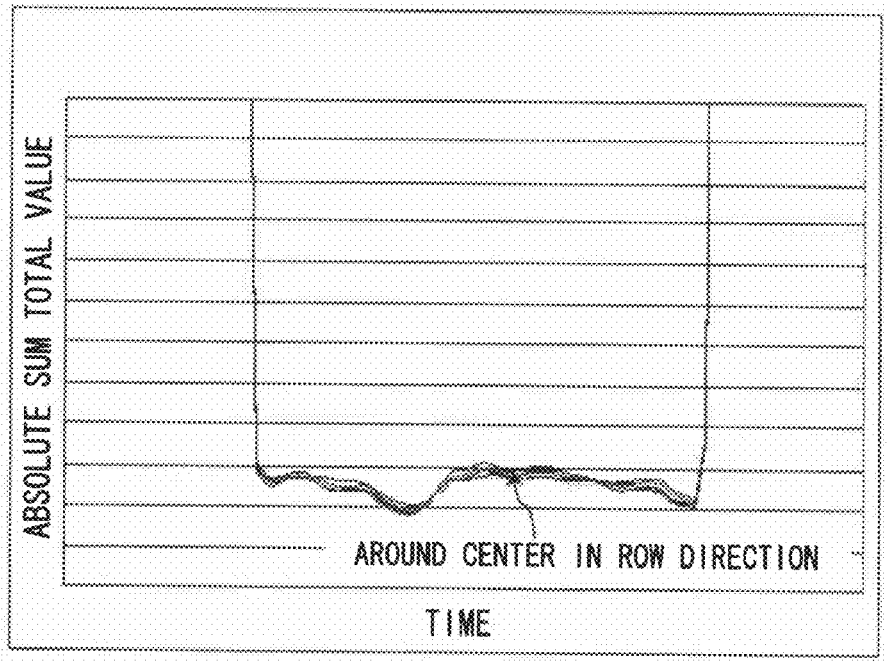
FIG. 8 is an exemplary time profile showing a second sample of an absolute sum total value for each row.

FIG. 8 is a time profile showing a second sample of the absolute sum total value for each row. The absolute sum total value of the absolute sum total value of 16-row X-ray detection elements 22a with the size of 0.5 mm×0.5 mm corresponding to the reference width WO (8 mm) in the row direction, which has been extracted from the time profile of the absolute sum total values for all rows as shown in FIG. 7 is calculated.

Each Y-axis of FIGS. 7 and 8 represents the absolute sum total value based on the difference data, and X-axis represents the time. Referring to FIG. 7, as the cone angle of the cone-beam X-ray irradiated from the X-ray tube 21 becomes large, that is, the row is located to the outer side of the X-ray detector 22 (especially the 1st row and the 84th row), the absolute sum total value is more likely to be influenced by the cone angle, thus failing to appropriately represent the motion amount. Accordingly, it is preferable to eliminate the projection data obtained via the X-ray detection element 22a in the row at the outer side so as not to be subjected to the accumulation process executed by the accumulation processing unit 56.

Meanwhile, Referring to FIG. 8, the X-ray detection element 22a of the X-ray detector 22 around the center in the row direction (for example, the range within 8 mm if the center in the row direction is centrally located) is hardly influenced by the cone angle (time profile substantially accorded). So, the projection data via the X-ray detection element 22a around the center in the row direction are only subjected to the accumulation process executed by the accumulation processing unit 56. This allows the absolute sum total value ST[n] of the optimum phase determination unit 57 to appropriately represent the motion amount. The profiles in FIGS. 7 and 8 show that it is preferable to set the region which centrally locates the center of the X-ray detector 22 in the row direction within 8 mm to the reference width WO by the accumulation processing unit 56 in the case where the X-ray detection element 22a has the size of 0.5 mm×0.5 mm.

The optimum phase determination unit 57 shown in FIG. 3 has a function to select the minimum absolute sum total value ST[m] from the absolute sum total values ST[1]-ST[50] for each calculated n in the case where the heartbeat phase variable m (m<=n) corresponds to the state of the motion with the lowest oscillation. For example, the minimum absolute sum total value ST[m] is originated from the projection data sets P[m] and P[m−2]. In other words, it represents that the cardiac motion becomes the lowest or nearly lowest in the range of the heartbeat phase from (2×(m−2)) % to (2×(m)) % in the single heartbeat cycle. The optimum phase determination unit 57 determines the optimum heartbeat phase by the following expression (1).

$$\{(2\times(m-2))\% + (2\times m)\%\}/2 \tag{1}$$

Note that the optimum phase determination unit 57 is allowed to determine the heartbeat phase at (2×(m−2)) % or ((2×m) %)/2 as the optimum phase besides the use of the above expression.

The optimum phase determination unit 57 is capable of displaying the information derived from correlating the heartbeat phase and the motion amount on the monitor of the display device 46. The optimum phase determination unit 57 reconstructs the image based on the determined optimum phase, and displays the resultant image on the monitor.

As described above, the optimum phase determination unit 57 determines the optimum phase by processing the projection data prior to the reconstruction process rather than the use of the reconstructed image, thus reducing the number of the process steps to the greater degree.

Figure 9:
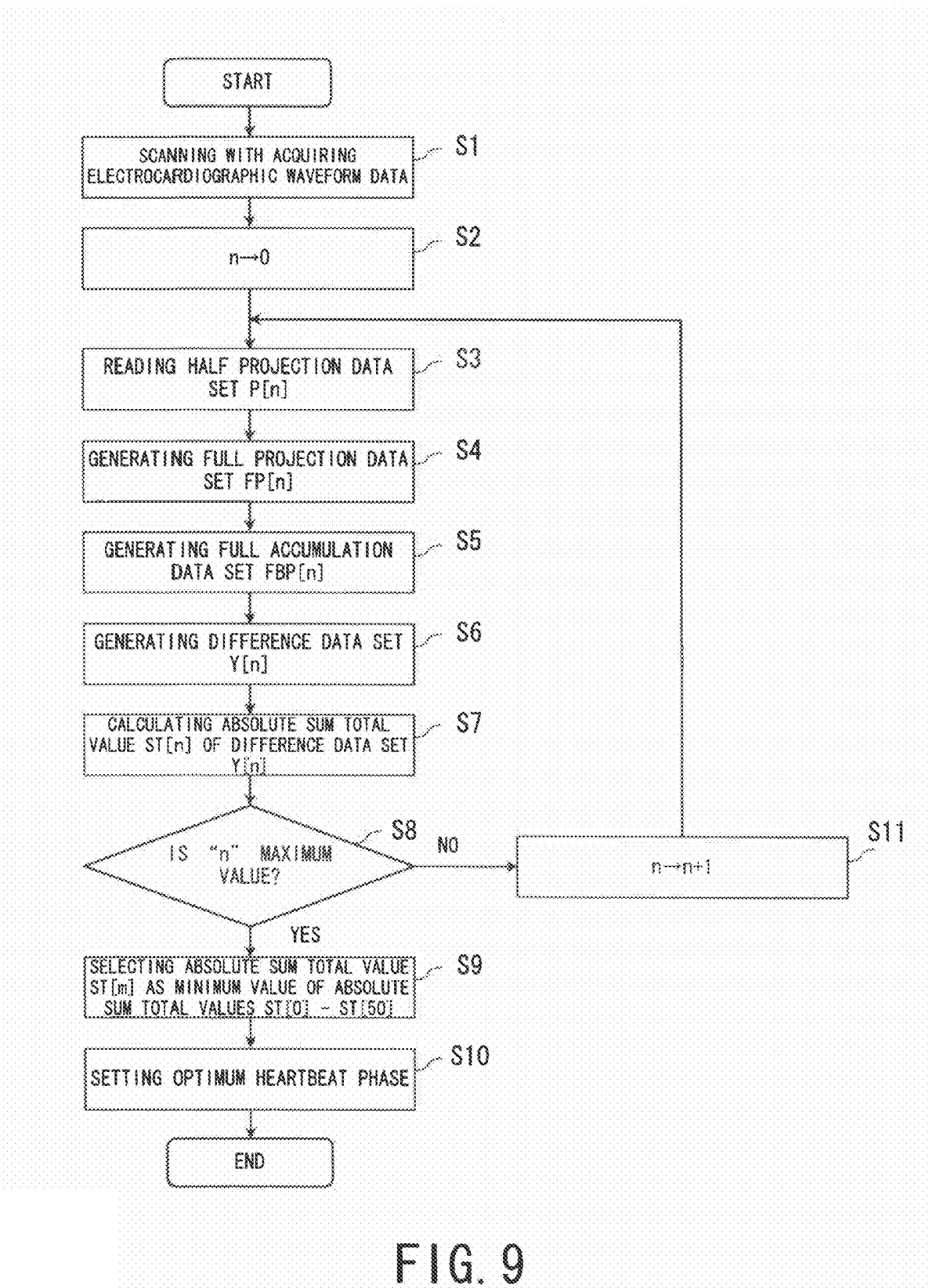
FIG. 9 is a flowchart showing an operation of the X-ray CT apparatus according to the first embodiment.

A operation of the X-ray CT apparatus 10 according to the first embodiment will be described referring to a flowchart shown in FIG. 9.

Under the control of the scan control unit 51, the scanning is executed while acquiring the electrocardiographic waveform data (step S1). The projection data for the duration corresponding to at least the single heartbeat are collected and stored in the data storage unit such as the HD 43. After the scanning, the operation for determining the optimum phase is started.

For the purpose of determining the optimum phase, the variable n for simply identifying the heartbeat phase is updated to 0 (step S2).

The half projection data set P[0] at (180°+α) around the heartbeat phase variable of 0% as the center is read from the data storage unit such as the HD 43 (step S3). In other words, the half projection data set P[0] around the heartbeat phase variable of 0% as the center is extracted from the series of data on the time-axis collected by the scanning in step S1.

The half projection data set P[0] is subjected to the 2D filter using the so-called parker 2D weighting factor map to generate the full projection data set FP[0] at 360° with the compensated difference of the number of the backprojection performed for each pixel with the heartbeat phase variable of 0% (step S4).

The required width of the X-ray detector 22 in the row direction is set, which is relatively insusceptible to the influence of the cone angle of the cone-beam X-ray. Based on the full projection data set FP[0] generated in step S4, the first projection data based on the first X-ray detection element 22a1 within the set required width W is subjected to the accumulation process with the same channel in the row direction in preference to the second projection data based on the second X-ray detection element 22a2 outside the required width W. As a result, the full accumulation data set FBP[0] with the heartbeat phase variable of 0% may be generated (step S5).

The difference between the full accumulation data set FBP[0] generated in step S5 and the two-phase previous full accumulation data set FBP[−2] is obtained together with the views and the channels to generate the difference data set Y[0] with the heartbeat phase variable of 0% (step S6).

Based on the difference data with respect to all the channels for forming the difference data set Y[0] generated in step S6, the absolute sum total value ST[0] with the heartbeat phase variable of 0 is calculated (Step S7).

It is determined whether or not the heartbeat phase variable n processed in steps S3 to S7 is a maximum value (n=50)(step S8). If YES is obtained in step S8, that is, it is determined that the heartbeat phase variable n is the maximum value, the absolute sum total value ST[m] for the heartbeat phase variable m is selected as the minimum value of the absolute sum total values ST[0]-ST[50] based on the difference data calculated in step S7 (step S9). The heartbeat phase corresponding to the minimum absolute sum total value ST[m] selected in step S9 is obtained by calculating the expression (1), for example. The obtained heartbeat phase is set as the optimum heartbeat phase (Step S10).

Meanwhile, if NO is obtained in step S8, that is, it is determined that the heartbeat phase variable n is not the maximum value, the value n processed in steps S3 to S7 is set to (n+1)(step S11), and the process returns to step S3. The process in steps S3 to S7 is repeatedly executed via the process in step S11 until the heartbeat phase variable n is maximized in the heartbeat duration.

In the X-ray CT apparatus 10 according to the first embodiment, the optimum heartbeat phase is set on the basis of only the first projection data based on the first X-ray detection element 22a1 within the required width W which is relatively insusceptible to the influence of the cone angle. This makes it possible to accurately set the optimum heartbeat phase with precision.

Figure 10:
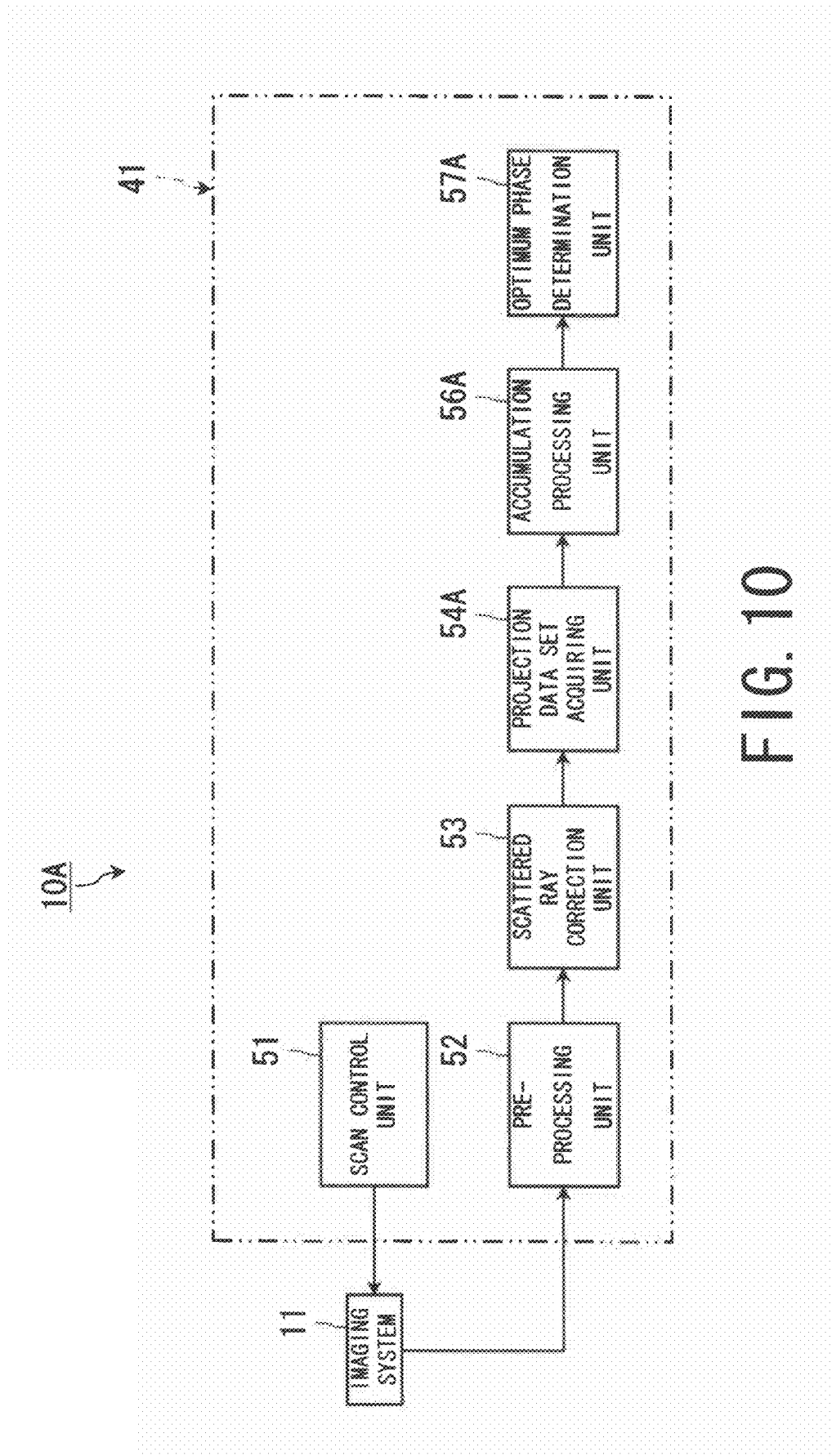
FIG. 10 is a block diagram showing functions of the X-ray CT apparatus according to a second embodiment.

FIG. 10 is a block diagram showing functions of an X-ray CT apparatus 10A according to a second embodiment. Note that the hardware structure of the X-ray CT apparatus 10A according to the second embodiment is the same as that of the X-ray CT apparatus 10 according to the first embodiment shown in FIG. 1, and the explanation thereof, thus will be omitted.

Upon execution of the program by the CPU 41 shown in FIG. 1, the X-ray CT apparatus 10A functions as the scan control unit 51, the pre-processing unit 52, the scattered ray correction unit 53, a projection data set acquiring unit 54A, an accumulation processing unit 56A, and an optimum phase determination unit 57A as shown in FIG. 10. In the following description, the respective units 51 to 57A for forming the X-ray CT apparatus 10A are activated by the CPU 41 for executing the program. However, the present invention is not limited to the aforementioned structure. All or a part of the units 51 to 57A for forming the X-ray CT apparatus 10A may be installed in the X-ray CT apparatus 10 as the hardware. The same elements of the X-ray CT apparatus 10A shown in FIG. 10 as those of the X-ray CT apparatus 10 shown in FIG. 3 will be designated as the same reference numerals, and explanations thereof, thus will be omitted.

The projection data set acquiring unit 54A has a function to acquire a full projection data set F'P[n] at 360° around the heartbeat phase variable n as the center from the projection data generated by the scattered ray correction unit 53. In other words, the projection data set acquiring unit 54 extracts the full projection data set F'P[n] at 360° around the heartbeat phase variable n as the center from the series of data on the time-axis collected through the scanning. In the following description, the projection data set acquiring unit 54A extracts the data corresponding to the single heartbeat duration. However, the projection data for plural different heartbeat durations corresponding to the heartbeat phase may be synthesized to generate the projection data for forming the single image.

The accumulation processing unit 56A includes a function to set the required width W likewise the accumulation processing unit 56, and a function to generate a full accumulation data set F'BP[n] at 360° by subjecting the first projection data based on the first X-ray detection element 22a1 within the set required width W to the accumulation process with the same channel in the row direction in preference to the second projection data based on the second X-ray detection element 22a2 outside the required width W on the basis of the full projection data F'P[n] at 360° acquired by the projection data set acquiring unit 54A.

For example, the accumulation processing unit 56A sets the weighting to the second projection data based on the second X-ray detection element 22a2 to 0, and accumulates only the first projection data based on the first X-ray detection element 22a1 in the row direction. Alternatively, the accumulation processing unit 56A applies a relatively large weighting to the first projection data based on the first X-ray detection element 22a1, and applies a relatively small weighting to the projection data based on the second X-ray detection element 22a2 so as to accumulate the weighted data in the row direction.

The optimum phase determination unit 57A has a function to determine the optimum phase based on the full accumulation data set F'BP[n] generated by the accumulation processing unit 56A. Specifically, the optimum phase determination unit 57A obtains difference data between the full accumulation data set F'BP[n] generated by the accumulation processing unit 56A and opposite data set formed of opposite data of the projection data for forming the full accumulation data set F'BP[n] to generate a difference data set Y'[n] as the difference data group. Note that the term "opposite data" represents the projection data having the line (projection line) formed by connecting the focus of the X-ray tube 21 and the channel center of the X-ray detector 22 overlapped with the one of the certain projection data.

Figure 11:
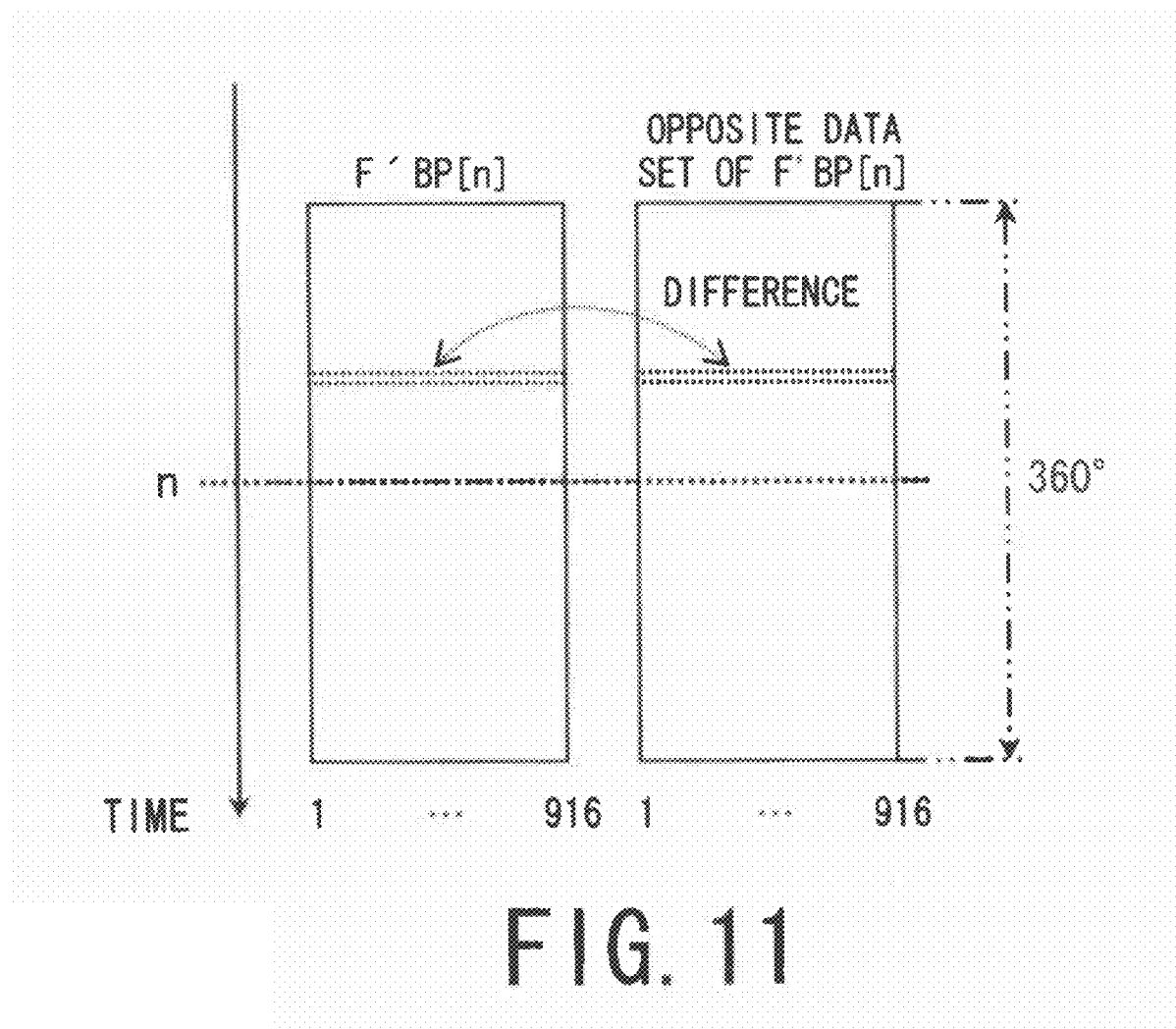
FIG. 11 is a diagram showing an example of a relationship between full accumulation data set and opposite data set, and the time.

FIG. 11 is a diagram showing an example of a relationship between the full accumulation data set F'BP[n], and the opposite data set, and the time.

The Y-axis of the graph shown in FIG. 11 represents the time (view for each data set), and the X-axis represents the channel direction of the X-ray detector 22. The optimum phase determination unit 57A calculates the difference between the full accumulation data set F'BP[n] and the opposite data set shown in FIG. 11 for each channel.

Besides the absolute sum total value based on the difference data for forming the difference data set Y'[n], the value indicating the motion amount may be obtained through the other method. For example, the width region corresponding to the ROI may be localized to calculate the sum total value.

Alternatively, the square sum may be employed rather than simple use of the absolute sum total value.

The optimum phase determination unit 57A is capable of displaying the information which represents the heartbeat phase correlated with the motion amount on the display device 46. The optimum phase determination unit 57A reconstructs the image based on the determined optimum phase, and displays the resultant image on the display device 46.

Figure 12:
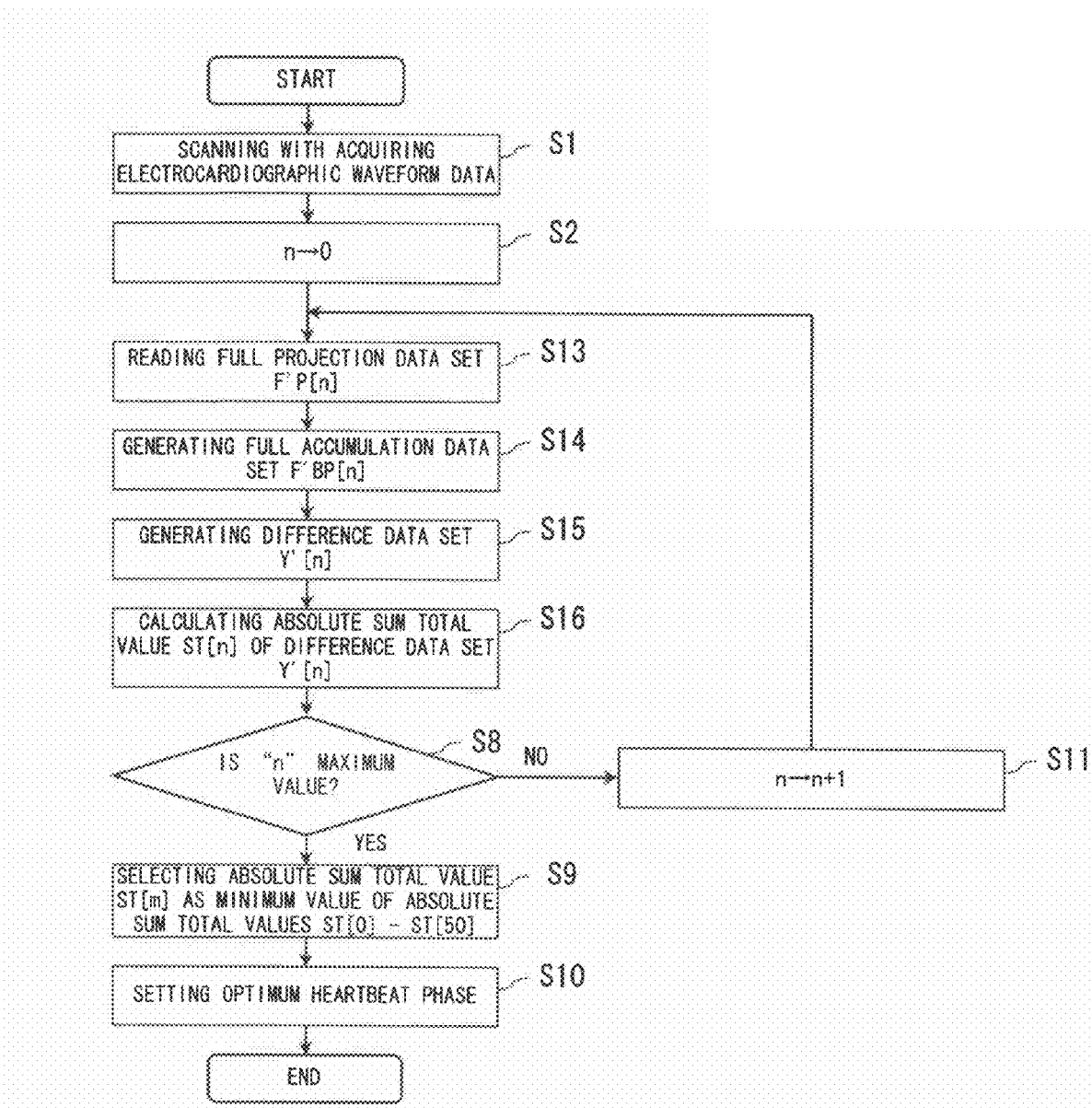
FIG. 12 is a flowchart showing an operation of the X-ray CT apparatus according to the second embodiment.

The operation of the X-ray CT apparatus 10A according to the second embodiment will be described referring to the flowchart shown in FIG. 12. In the operation of the X-ray CT apparatus 10A shown in FIG. 12, the same steps as those of the operation of the X-ray CT apparatus 10 shown in FIG. 9 will be designated with the same numbers, and explanations thereof, thus will be omitted.

Subsequent to step S2, the full projection data set F'P[0] at 360° around the heartbeat phase variable of 0% as the center is read from the data storage unit such as the HD 43 (step S13). In other words, the full projection data set F'P[0] at 360° around the heartbeat phase variable of 0% as the center is extracted from the series of data on the time-axis collected through the scanning in step S1.

The required width W which is relatively insusceptible to the influence of the cone angle of the cone-beam X-ray is set in the row direction of the X-ray detector 22. On the basis of the full projection data set F'P[0] at 360° read in step S13, the first projection data based on the first X-ray detection element 22a1 within the set required width are subjected to the accumulation process with the same channel in the row direction in preference to the second projection data based on the second X-ray detection element 22a2 outside the required width so as to generate the full accumulation data set F'BP[0] with the heartbeat phase variable of 0% (Step S14).

The difference data between the full accumulation data set F'BP[0] generated in step S14 and the opposite data set formed of opposite data of the projection data for forming the full accumulation data set F'BP[0] are obtained to generate the difference data set Y'[0] with the heartbeat phase variable of 0% (step S15).

Based on the difference data for all the channels for forming the difference data set Y'[0] generated in step S15, the absolute sum total value ST[0] with the heartbeat phase variable of 0% is calculated (step S16).

It is determined whether or not the heartbeat phase variable n processed in steps S13 to S16 is a maximum value (n=50) (step S8). If NO is obtained in step S8, that is, it is determined that the heartbeat phase variable n is not the maximum value, the variable n processed in steps S13 to S16 is set to (n+1) (step S11), and the process returns to step S13. The process in steps S13 to S16 is repeatedly executed via the process in step S11 until the heartbeat phase variable n is maximized in the heartbeat duration.

In the X-ray CT apparatus 10A according to the second embodiment, the optimum heartbeat phase is set on the basis of only the first projection data based on the first X-ray detection element 22a1 within the required width W which is relatively insusceptible to the influence of the cone angle. This makes it possible to accurately set the optimum heartbeat phase with precision.

What is claimed is:
1. An X-ray CT apparatus comprising:
   an X-ray tube configured to irradiate a cone-beam X-ray to an object;
   an X-ray detector, configured to detect the X-ray, including a group of plural X-ray detection elements arrayed in a matrix;
   an electrocardiogram configured to measure a heartbeat phase of the object;
   a set unit configured to set a required width of the group of the X-ray detection elements in a row direction, which is relatively insusceptible to an influence of a cone angle of the cone-beam X-ray;
   a generation unit configured to generate accumulation data by accumulating first projection data, based on first X-ray detection elements within the required width included in the group, with same channel in the row direction in preference to second projection data based on second X-ray detection elements outside the required width included in the group;
   a calculation unit configured to obtain a motion amount for each heartbeat phase measured by the electrocardiogram based on the accumulation data; and
   a determination unit configured to determine a specific heartbeat phase based on the motion amount for the each heartbeat phase.

2. The X-ray CT apparatus according to claim 1, further comprising a display device configured to display information with respect to the heartbeat phase correlated with the motion amount.

3. The X-ray CT apparatus according to claim 1, further comprising a display device configured to display an image reconstructed based on the specific heartbeat phase determined by the determination unit.

4. The X-ray CT apparatus according to claim 1, wherein the set unit obtains difference data between projection data with corresponding views, channel numbers and row numbers in two full projection data sets at 360° with different heartbeat phases, and sets the required width to include the row having a time profile indicating an absolute sum total value for each row based on the difference data substantially accorded.

5. The X-ray CT apparatus according to claim 1, wherein the calculation unit includes;
   a unit configured to form a full accumulation data set as the accumulation data at 360°, and provide difference data between the accumulation data with corresponding views and channel numbers in the two full accumulation data sets with different heartbeat phase variables; and
   a unit configured to calculate an absolute sum total value based on the difference data as the motion amount.

6. The X-ray CT apparatus according to claim 1, wherein the calculation unit obtains difference data between required accumulation data and opposite data based on a full accumulation data set as the accumulation data at 360°, and calculates the motion amount based on a difference data set as a group of the difference data.

7. The X-ray CT apparatus according to claim 1, wherein the generation unit accumulates only the first projection data in the row direction.

8. The X-ray CT apparatus according to claim 1, wherein the generation unit applies a larger weighting to the first projection data, and applies a smaller weighting to the second projection data to accumulate the weighted data in the row direction.

9. The X-ray CT apparatus according to claim 1, wherein the set unit sets the require width so as to centrally locate a center in the row direction.

10. The X-ray CT apparatus according to claim 9, wherein the set unit sets the required width to be equal to 8 mm or smaller.

11. A control method of an X-ray CT apparatus comprising:
- a setting step of setting a required width of a group of X-ray detection elements in a row direction, which is relatively insusceptible to an influence of a cone angle of a cone-beam X-ray;
- a generating step of generating accumulation data by accumulating first projection data, based on first X-ray detection elements within the required width included in the group, with same channel in the row direction in preference to second projection data based on second X-ray detection elements outside the required width included in the group;
- a calculation step of obtaining a motion amount for each of measured heartbeat phases based on the accumulation data; and
- a determination step of determining a specific heartbeat phase based on the motion amount for the each heartbeat phase.

12. The control method according to claim 11, further comprising a display step of displaying information with respect to the heartbeat phase correlated with the motion amount.

13. The control method according to claim 11, further comprising a display step of displaying an image reconstructed based on the specific heartbeat phase determined by the determination step.

14. The control method according to claim 11, wherein the setting step obtains difference data between projection data with corresponding views, channel numbers and row numbers in two full projection data sets at 360° with different heartbeat phases, and sets the required width to include the row having a time profile indicating an absolute sum total value for each row based on the difference data substantially accorded.

15. The control method according to claim 11, wherein the calculation step includes;
- a step of forming a full accumulation data set as the accumulation data at 360°, and providing difference data between the accumulation data with corresponding views and channel numbers in the two full accumulation data sets with different heartbeat phase variables; and
- a step of calculating an absolute sum total value based on the difference data as the motion amount.

16. The control method according to claim 11, wherein the calculation step obtains difference data between required accumulation data and opposite data based on a full accumulation data set as the accumulation data at 360°, and calculates the motion amount based on a difference data set as a group of the difference data.

17. The control method according to claim 11, wherein the generation step accumulates only the first projection data in the row direction.

18. The control method according to claim 11, wherein the generation step applies a larger weighting to the first projection data, and applies a smaller weighting to the second projection data to accumulate the weighted data in the row direction.

19. The control method according to claim 11, wherein the setting step sets the require width so as to centrally locate a center in the row direction.

20. The control method according to claim 19, wherein the setting step sets the required width to be equal to 8 mm or smaller.

* * * * *